United States Patent
Barr et al.

(10) Patent No.: US 7,089,982 B2
(45) Date of Patent: Aug. 15, 2006

(54) APPARATUS FOR CONSTRUCTING A CAPACITOR STACK FOR A FLAT CAPACITOR

(75) Inventors: Alexander Gordon Barr, Burnsville, MN (US); Paul K. Hamre, Stillwater, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 0 days.

(21) Appl. No.: 10/637,604

(22) Filed: Aug. 8, 2003

(65) Prior Publication Data

US 2004/0029302 A1 Feb. 12, 2004

Related U.S. Application Data

(62) Division of application No. 10/050,598, filed on Jan. 15, 2002, now Pat. No. 6,632,720.

(51) Int. Cl.
*B32B 41/00* (2006.01)

(52) U.S. Cl. .................. 156/358; 156/362; 156/363; 156/378; 156/379

(58) Field of Classification Search ............... 156/379, 156/563, 559, 564, 565, 378, 358, 362, 363, 156/364; 100/266, 267, 268, 45; 29/25.03; 414/789.9, 720, 790.2
See application file for complete search history.

(56) References Cited

U.S. PATENT DOCUMENTS

| | | | |
|---|---|---|---|
| 4,553,304 A | 11/1985 | Fleuret | 29/25.42 |
| 4,683,516 A | 7/1987 | Miller | 361/328 |
| 5,522,851 A | 6/1996 | Fayram | 607/5 |
| 5,628,801 A | 5/1997 | MacFarlane et al. | 29/25.03 |
| 5,640,756 A | 6/1997 | Brown et al. | 29/701 |
| 5,814,082 A | 9/1998 | Fayram et al. | 607/5 |
| 5,908,151 A | 6/1999 | Elias | 228/110.1 |
| 5,983,472 A | 11/1999 | Fayram et al. | 29/25.42 |
| 6,006,133 A | 12/1999 | Lessar et al. | 607/5 |
| 6,030,480 A | 2/2000 | Face, Jr. et al. | 156/160 |
| 6,042,624 A * | 3/2000 | Breyen et al. | 29/25.03 |
| 6,110,321 A | 8/2000 | Day et al. | 156/286 |
| 6,141,205 A | 10/2000 | Nutzman et al. | 361/509 |
| 6,233,135 B1 * | 5/2001 | Farahmandi et al. | 361/502 |
| 6,402,793 B1 | 6/2002 | Miltich et al. | 29/25.03 |
| 6,413,283 B1 | 7/2002 | Day et al. | 29/25.3 |
| 6,509,588 B1 | 1/2003 | O'Phelan et al. | 257/209 |
| 6,522,525 B1 | 2/2003 | O'Phelan et al. | 361/509 |

(Continued)

FOREIGN PATENT DOCUMENTS

WO    WO98/51602    * 11/1998

OTHER PUBLICATIONS

IBM Technical Disclosure Bulletin NN81024261, "Clamping Mechanism", Feb. 1, 1981, vol. 23, Issue 9, pp. 4261-4263.*

*Primary Examiner*—George Koch
(74) *Attorney, Agent, or Firm*—Schwegman, Lundberg, Woessner & Kluth, P.A.

(57) ABSTRACT

A method of manufacturing a capacitor stack for a flat capacitor includes sequentially stacking a plurality of capacitor layers on top of each other such that each one of the plurality of capacitor layers is, in turn, a top layer of the capacitor stack, and continually applying a compression force between a bottom layer of the capacitor stack and the top layer of the capacitor stack until all of the plurality of capacitor layers have been placed.

9 Claims, 6 Drawing Sheets

U.S. PATENT DOCUMENTS

| | | |
|---|---|---|
| 6,833,987 B1 | 12/2004 | O'Phelan |
| 2001/0020319 A1 | 9/2001 | Farahmandi et al. ........ 29/25.03 |
| 2004/0114311 A1 | 6/2004 | O'Phelan et al. |
| 2004/0127952 A1 | 7/2004 | O'Phelan et al. .............. 607/36 |
| 2004/0147960 A1 | 7/2004 | O'Phelan et al. |
| 2004/0147961 A1 | 7/2004 | O'Phelan et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2005/0010253 A1 | 1/2005 | O'Phelan et al. |
| 2005/0017888 A1 | 1/2005 | Sherwood et al. |
| 2005/0052825 A1 | 3/2005 | O'Phelan |

* cited by examiner

APPARATUS FOR CONSTRUCTING A CAPACITOR STACK FOR A FLAT CAPACITOR

CROSS-REFERENCE TO RELATED APPLICATION(S)

This application is a division of U.S. patent application Ser. No. 10/050,598, filed on Jan. 15, 2002, now issued as U.S. Pat. No. 6,632,720, the specification of which is incorporated herein by reference.

TECHNICAL FIELD

The present invention concerns capacitors for implantable medical devices, such as defibrillators and cardioverters, and more specifically to a method of manufacturing a capacitor stack for a flat capacitor.

BACKGROUND

Implantable defibrillators detect the onset of abnormal heart rhythms and apply corrective electrical therapy, specifically one or more bursts of electric current to the heart. A defibrillator includes a set of electrical leads, which extend from a pulse generator housing into the heart. Within the pulse generator housing are a battery for supplying power, monitoring circuitry for detecting abnormal heart rhythms, and a capacitor for delivering the bursts of electric current through the leads to the heart. Since defibrillators are usually implanted in the left region of the chest or in the abdomen, a smaller size device, which is still capable of delivering the required level of electrical energy, is desirable. Accordingly, smaller and more powerful capacitors are desirable.

One type of capacitor is a flat capacitor. Flat capacitors have a layered stack of capacitor elements. The stack includes a series of anode and cathode foil layers each separated by a separator layer. To ensure that a capacitor stack does not short out and that it takes up as little volume as possible it is important to carefully align each layer of the capacitor stack when constructing the capacitor stack.

SUMMARY

The present system includes methods and apparatus to manufacture a capacitor stack so the stack is precisely aligned while optimizing the area and volume of the stack.

In one embodiment, a method of manufacturing a capacitor stack for a flat capacitor includes sequentially stacking a plurality of capacitor layers on top of each other such that each one of the plurality of capacitor layers is, in turn, a top layer of the capacitor stack, and continually applying a compression force between a bottom layer of the capacitor stack and the top layer of the capacitor stack until all of the plurality of capacitor layers have been placed.

One aspect provides an apparatus for forming a capacitor stack. In one embodiment, an apparatus includes a fixture for holding a plurality of capacitor layers defining the capacitor stack as each of the plurality of capacitor layers is placed onto the capacitor stack, and means for continually applying a compression force on the capacitor stack until each of the plurality of capacitor layers have been stacked.

DESCRIPTION OF EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
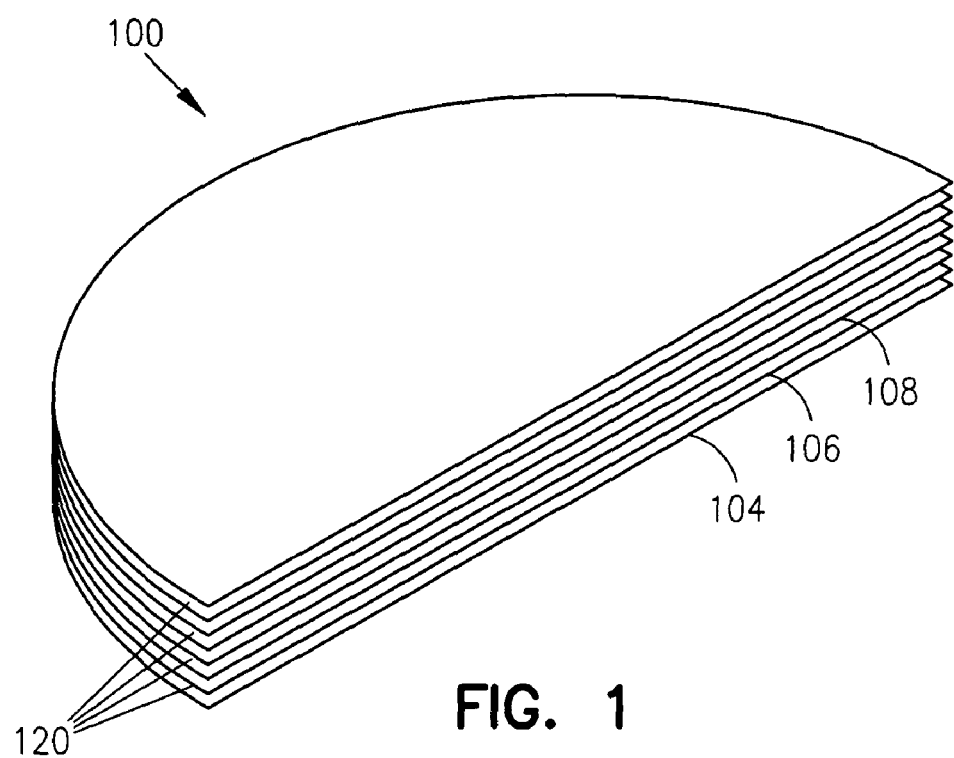
FIG. 1 is a perspective view of a flat capacitor stack manufactured in accordance with one embodiment.

In one embodiment, the present system is directed to manufacturing a capacitor stack for a flat capacitor. FIG. 1 shows an example of a flat capacitor stack 100. The present example shows a D-shaped capacitor stack. In other examples, capacitor stack 100 can be designed in a variety of flat shapes to conform to various housing shapes. The capacitor stack is mountable within a conforming metallic capacitor case with feedthroughs passing through the case to connect the capacitor to outside circuitry.

Capacitor stack 100 includes a plurality of capacitor layers 102. Each of layers 102 can be an anode layer 104, a cathode layer 106, or a separator layer 108. Each anode layer 104 can include 1, 2, 3 or more anode foils in a multi-foil anode configuration. The anode and cathode layers 104 and 106 comprise foils of aluminum, tantalum, hafnium, niobium, titanium, zirconium, butrylactone, or combinations of these metals. Separators 108 separate each anode layer 104 from each cathode layer 106 and carry an electrolyte such as an ethylene-glycol base combined with butrylactone. Separators 108 can be made from pure cellulose or Kraft paper. Separator 108 can be cut slightly larger than the anode layers and the cathode layers to prevent subsequent shorting between electrodes of opposite polarity.

Figure 2:
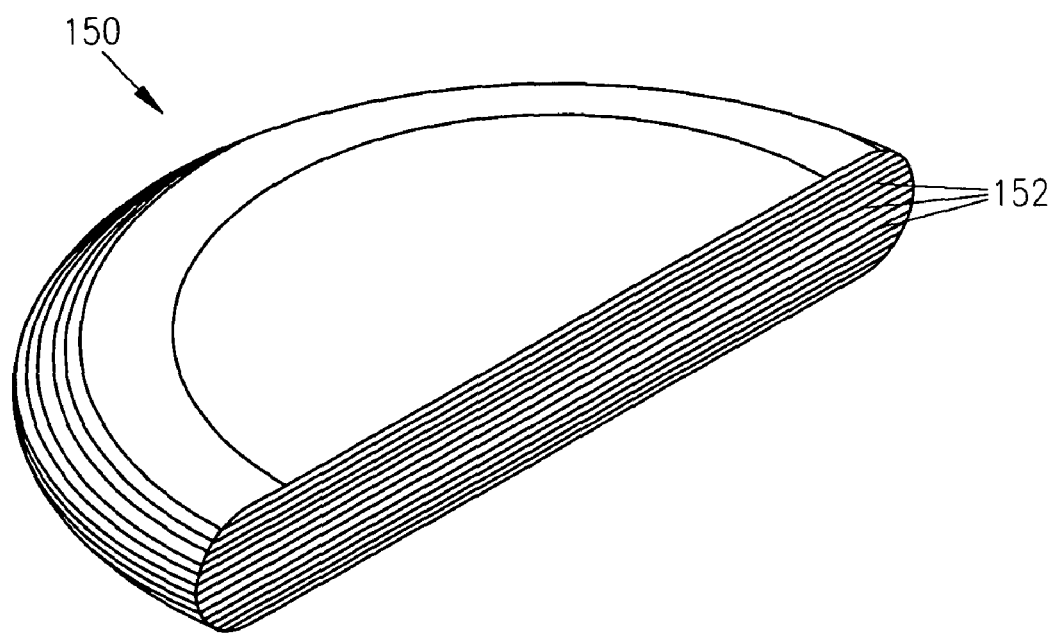
FIG. 2 is a perspective view of a flat capacitor stack manufactured in accordance with one embodiment.

FIG. 2 shows another example of a capacitor stack which can be manufactured in accordance with the present system. Capacitor stack 150 includes a plurality of capacitor layers 152 comprising anode foil layers, cathode foil layers, and separator layers. In this example, the surface area of the anode, cathode, and separator layers are staggered to define curved faces for the capacitor stack. This provides for a more shape efficient capacitor design for fitting in a curved defibrillator case. In other examples of a capacitor stack, the stack can take other forms having different numbers of anode and cathode layers and separators. The present method of manufacture of a capacitor stack is applicable to almost any arrangement of the stack and the previous are an example.

As noted above, each layer in a capacitor stack must be aligned correctly so the stack can fit within a capacitor case and so the adjacent elements do not contact each other and short out. This can be difficult, since each layer is thin and flimsy, making them difficult to stack. In the past, alignment features such as cut-outs on the foil layers or physical features in the capacitor case were used to help align the layers. However, these features themselves take up room that could be used for active electrode material. The present system includes a method and system for manufacturing a capacitor stack that does not require such alignment features.

Figure 3A:
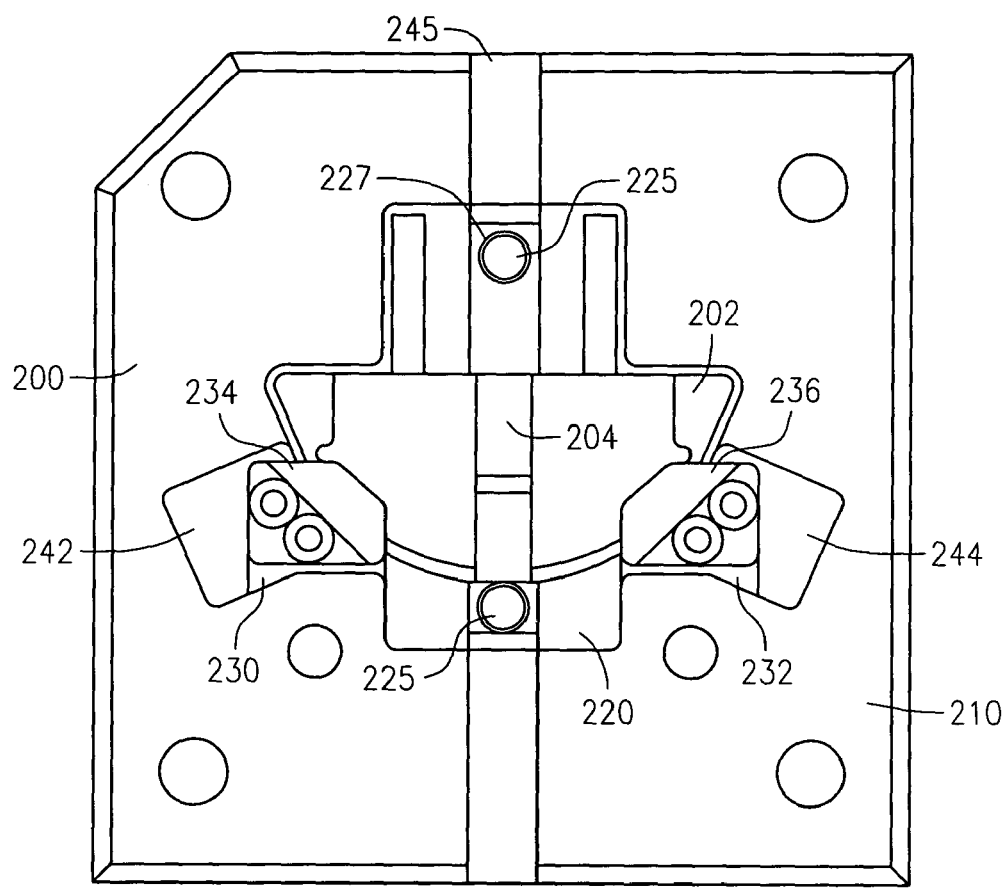
FIG. 3A is a top view of a capacitor stack assembly fixture according to one embodiment.
Figure 3B:
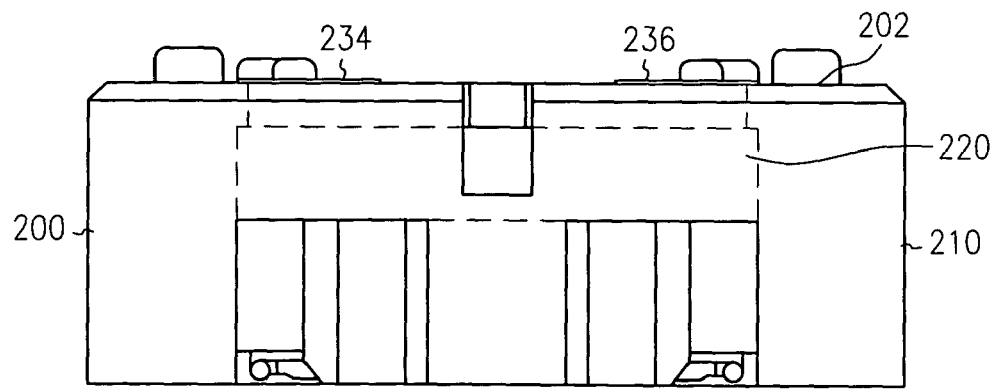
FIG. 3B is a front view of the fixture of FIG. 3A.
Figure 4:
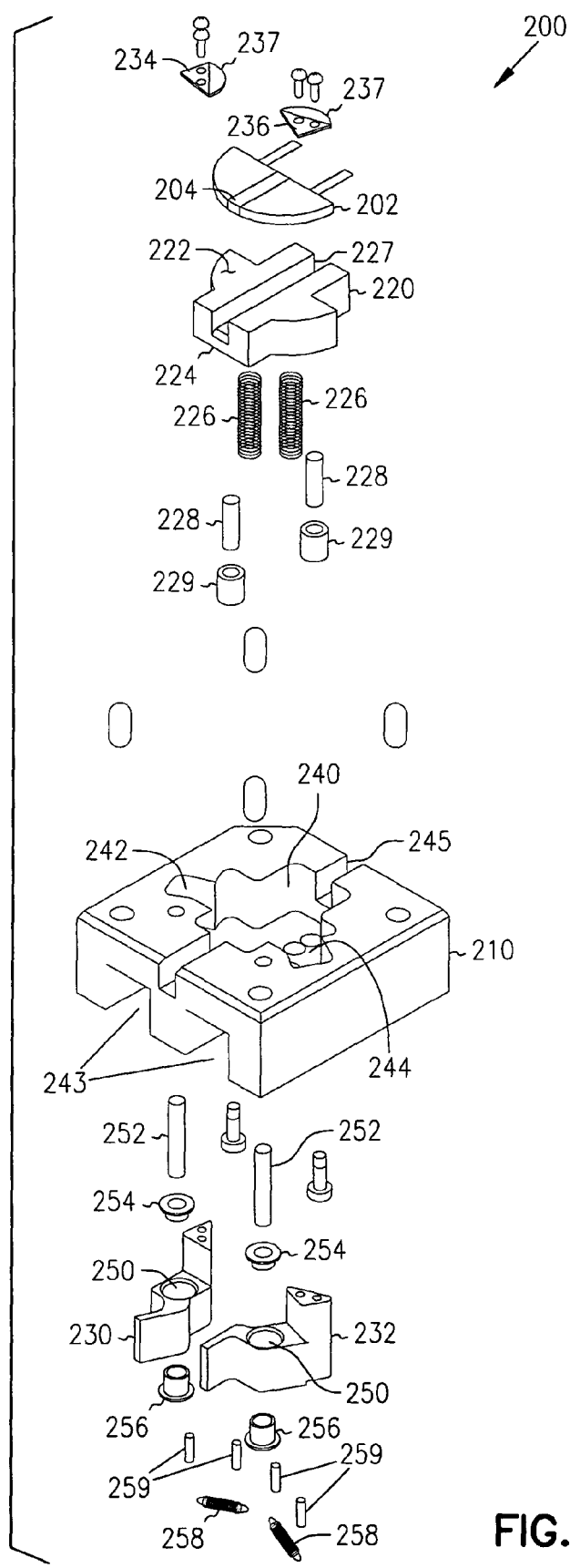
FIG. 4 is an exploded view of the fixture of FIGS. 3A and 3B.

FIGS. 3A, 3B, and 4 show a top, front, and exploded view, respectively, of a capacitor stack alignment fixture 200 in accordance with one embodiment. Fixture 200 generally includes a base 210, a base pad 220, first and second levers 230 and 232, and first and second upper members 234 and 236. In use, fixture 200 helps to continually keep all the layers of a capacitor stack in compression as the capacitor stack is being formed. In one embodiment, as will be detailed below, as each layer of a capacitor stack is placed upon base pad 220, the base pad urges the stack upward while upper members 234 and 236 provide a holding, downward force on the stack such that the stack is squeezed between base pad 220 and upper members 234 and 236. This squeezing or compression holds each layer of the capacitor stack in the position in which it was placed on the stack, thus keeping the alignment of the capacitor stack.

Base 210 includes an interior cavity 240. In one embodiment, interior cavity 240 is shaped to accommodate base pad 220 therein to allow the base pad to translate up and down. Base pad 220 and cavity 240 are shaped to accommodate example capacitor stack 202. As noted above, flat capacitors can be formed into almost any shape. Accordingly, base pad 220, although shown having a shape to accommodate the D-shape of the example capacitor stack 202, can have almost any shape. Cavity 240 includes side cavity portions 242 and 244 for accommodating levers 230 and 232 within base 210.

Base pad 220 includes a flat top surface 222 for supporting a bottom surface of capacitor stack 202. In one embodiment, the surface area of base pad surface 222 is slightly larger than the surface area of the capacitor stack. In one embodiment, a straight, longitudinal groove 227 is provided in the top surface of base pad 220. Along with a corresponding groove 245 in base pad 210, groove 227 provides a space for a binder such as a tape 204 to be laid into while a capacitor stack is being formed in fixture 200. After the stack is formed, tape 204 is wrapped around the capacitor stack to bind the stack and to hold the stack's alignment. Some embodiments omit groove 227, while other embodiments include a two-part base pad 220 in which groove 227 extends all the way through to the bottom surface of the base pad dividing the base pad into two parts. In one example, the finished stack is removed from the fixture, tape is wrapped around the middle of the stack, and then the stack is placed back in the fixture.

Fixture 200 includes one or more forcing or biasing members such as springs 226 which are located beneath base pad 220 to urge base pad 220 upward. In one example, base pad 220 includes one or more holes 225 having shafts 228 mounted therein. One or more bushings 229 are mounted in base 210 and aligned with shafts 228 so as to receive the shafts and to keep base pad 220 aligned as shafts 228 translate up and down within the bushings as base pad 220 is moved up and down within cavity 240.

Levers 230 and 232 are rotatably coupled to base 210 and used for moving upper members 234 and 236 in and out of cavity 240. In one embodiment, each lever 230 and 232 include a pivot hole 250. A shaft 252 and one or more bearings 254 and 256 can be mounted between each lever and base 210 to rotatably couple each lever to the base. In one example a spring 258 is coupled to each lever 230 and 232 by one or more pins 259 to bias each lever such that the levers are both urged inward. One or more openings 243 can be provided in a side of base 210 to provide access to levers 230 and 232. This allows the levers to be manually actuated by a user. In some embodiment, the levers can be actuated by mechanical drives or other means. Each lever extends to the top surface of base 210 and includes upper surfaces for mounting upper members 234 and 236 thereto.

In one embodiment, each upper member 234 and 236 is a thin, flat member having a back portion mounted to the lever and a front portion 237 which hangs over the edge of the lever. The front portion 237 is for contacting the top surface of a capacitor stack located within fixture 200 when the upper member 234 or 236 is located over the stack. In one example, a bottom surface of each upper member 234 and 236 is located substantially level with an upper surface of base 210 such that the top layer of a capacitor stack within fixture 200 is substantially even with the top surface of the fixture. The upper members 234 and 236 are dimensioned so that when lever 230 or 232 is rotated outwardly, the upper member 234 or 236 is not above the top surface of a capacitor stack located within fixture 200. In this example, the upper members 234 and 236 are located so as to contact the top side edges of a capacitor stack when the stack is being formed. This helps keep the edges of a given layer from curling up, as the thin layers have a tendency to do. This curling can be a cause of misalignment.

Figure 9:
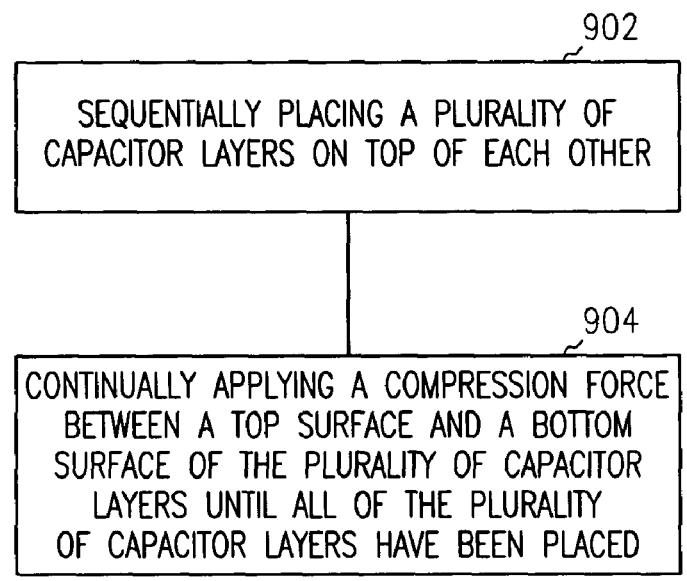
FIG. 9 depicts a flowchart of a method of constructing a capacitor stack in accordance with one embodiment.

FIGS. 5–8 show one example use of fixture 200 for forming a capacitor stack 100, while FIG. 9 shows a flowchart of a method 900, according to one embodiment, for constructing a capacitor stack. Method 900 includes sequentially placing a plurality of capacitor layers on top of each other (902), and continually applying a compression force between a top and a bottom surface of the plurality of capacitor layers until all of the plurality of capacitor layers have been placed (904). Method 900 will be understood in reference to the following discussion of FIGS. 5–8.

Figure 5:
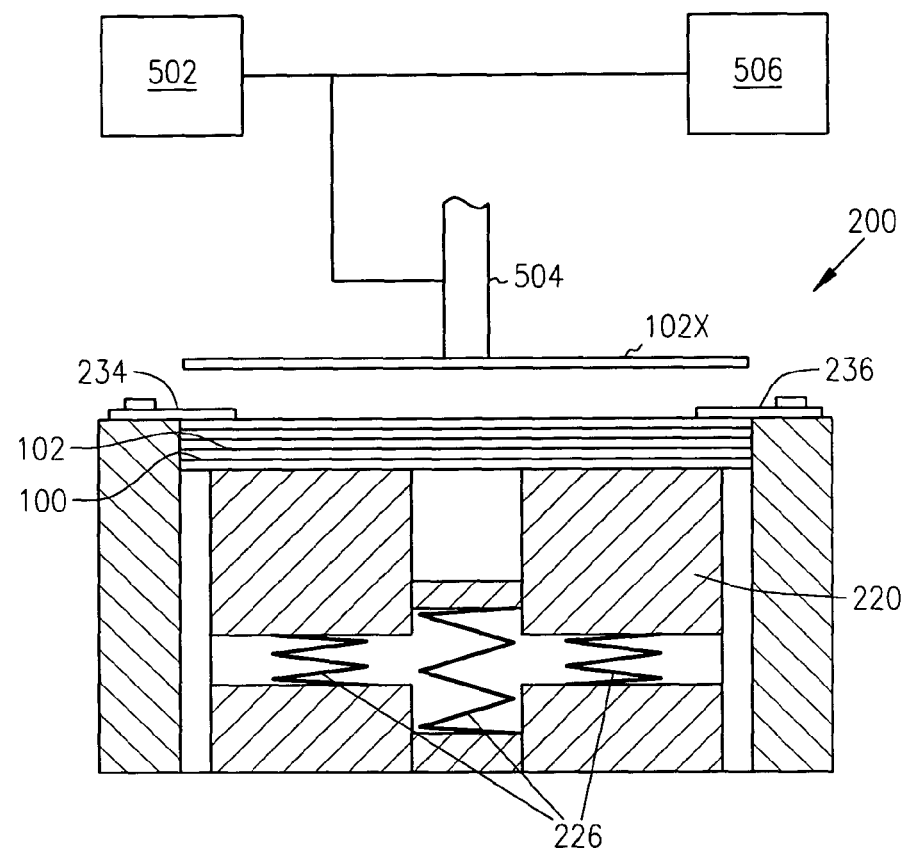
FIGS. 5–8 show schematic cross-section views of the fixture of FIG. 2 in one example use of the fixture.

In FIG. 5, a plurality of layers 102 of capacitor stack 100 are shown already mounted within fixture 200 while a new layer 102X is about to be placed upon the stack. Base pad 220 is urged upward by springs 226 forcing capacitor stack 100 into compression between the base pad and the bottom surfaces of upper members 234 and 236.

Springs 226 can be compression springs, leaf springs, or other biasing mechanisms which apply an upward force on the base pad. One or more springs 226 can be used to vary the amount of force as necessary. The overall force applied by the springs on the base pad increases as the stack grows larger. In one example, the spring force when the stack is empty is approximately 0 lbs. The force grows as the stack is formed until the force is approximately 2 lbs. when the base pad is fully depressed. In other examples, the high end force can range from ¼ lb. to approximately 3 lbs., approximately 4 lbs., or more, depending on the material being stacked. Also, the low-end force (i.e., when the stack is empty) can be varied. For example, a pre-load can be applied on the springs to urge the springs against the bottom of members 234 and 236 before any capacitor layers have been placed therein. This pre-load force can range from less than approximately ¼ lb, to approximately ¼ lb., approximately ½ lb., or more, depending on the application.

In this example, a controller 502 is shown coupled to a placement arm 504 and an alignment system 506. In one embodiment, placement arm 504 is a robotic arm for picking up and placing each layer of capacitor stack into the fixture. In other examples, placement arm 504 can be a manually controlled placement member or a tool held or controlled by user. In one embodiment, alignment system 506 is a computer-controlled vision alignment system. In use, such a vision system can be attached to placement member 504 and be calibrated to cause the arm to precisely position each layer when a reference point on the fixture is detected. In other embodiments, a user can use a microscope or other vision alignment system. In one embodiment, an ADEPT Technology robotics and vision system is used.

In the example shown, placement arm 504 includes a vacuum attachment for picking up each layer of the capacitor stack. Controller 502 controls placement arm 504 to precisely align each layer upon the stack with input from alignment system 506. Placement arm 504 is robotically translated from a pick-up position to deliver each layer to the stack. For sake of clarity, members 506 and 508 are not shown in FIGS. 6–8.

New capacitor layer 102X can be a single anode or cathode foil, a multi-foil anode member, a single or multi-sheet separator, or combinations of these layers. For instance, in some examples, a capacitor sub-assembly of an anode foil, separator, cathode foil is prepared, and then fixture 200 is used to stack, align, and manufacture those sub-assemblies into a capacitor stack. In some examples, each individual capacitor layer is individually put into fixture 200. Moreover, the present system can be used for forming a complete capacitor stack, such as stacks 100 or 150 of FIGS. 1 and 2, or for forming sub-assemblies of a capacitor stack, such as mentioned above.

Figure 6:
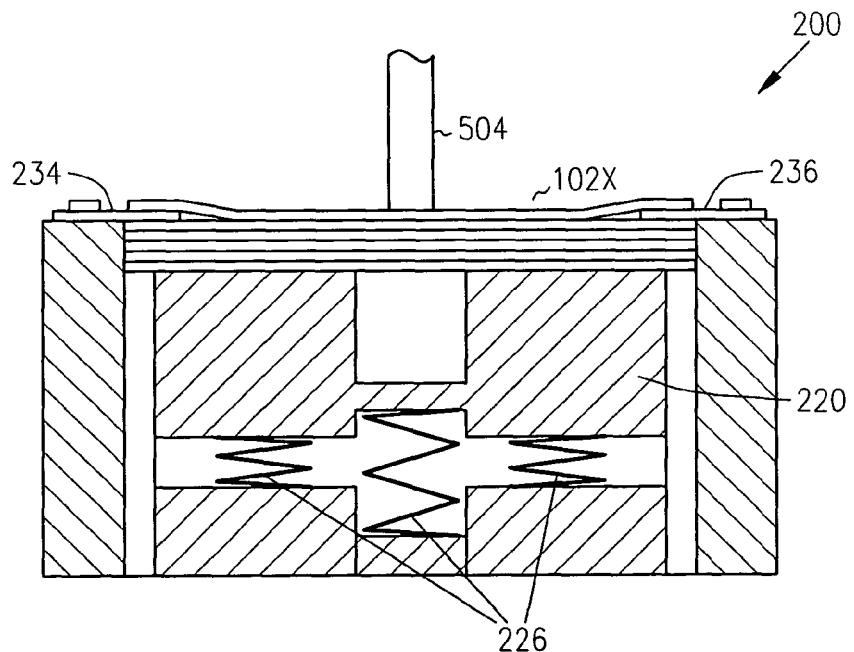

In FIG. 6, placement arm 504 is lowered until the top surface of new top layer 102X is approximately even with the bottom surface of upper members 234 and 236 while the edges of new layer 102X stay above upper member 234 and 236. Placement arm 504 holds the stack in compression against biased base pad 202, along with upper member 234 and 236.

Figure 7:
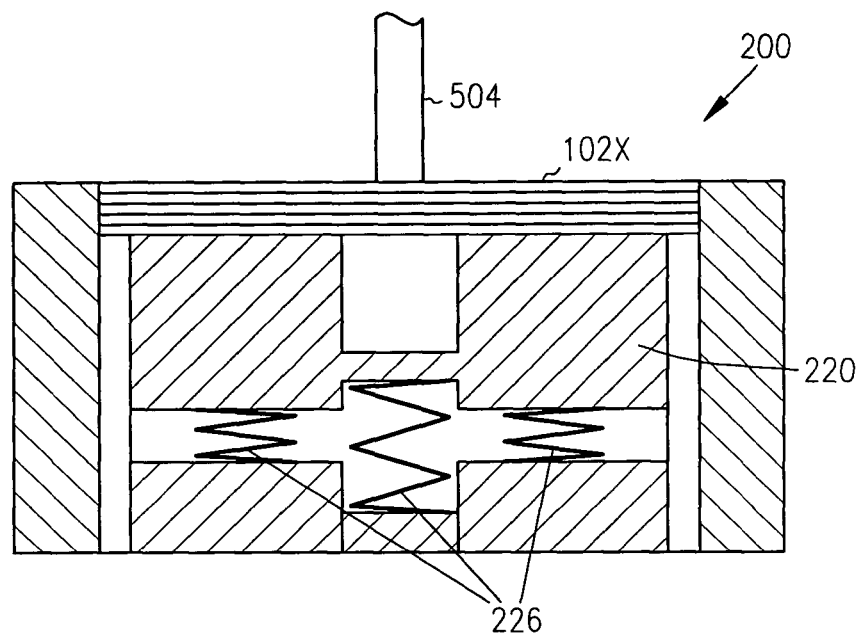
Figure 8:
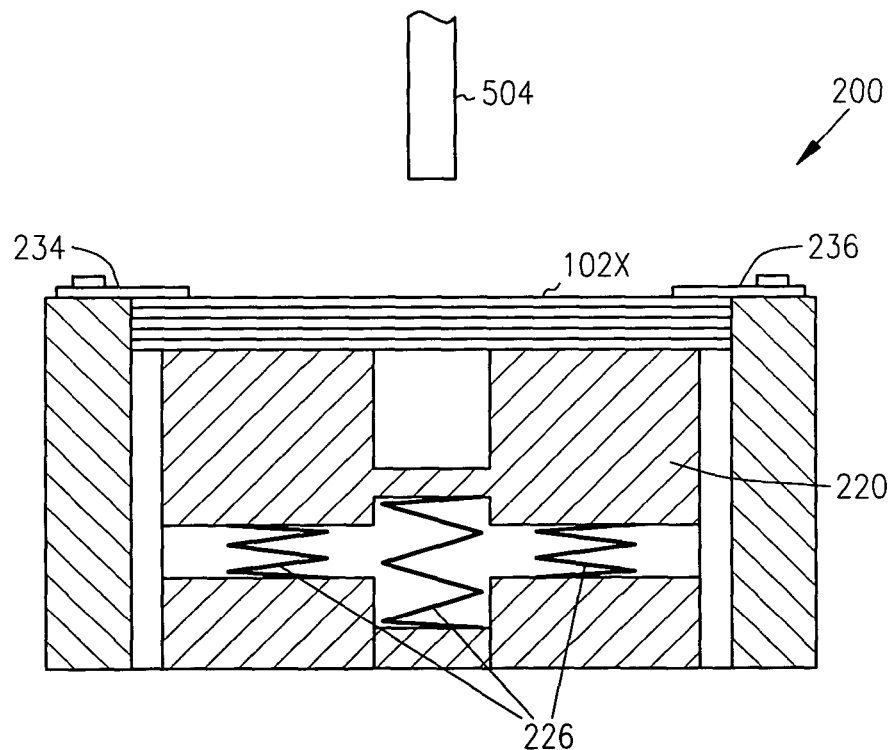

In FIG. 7, placement arm 504 remains in place as it was in FIG. 6, while upper members 234 and 236 are moved out of the way such that the edge surfaces of layer 102X which were above the upper members in FIG. 6 now fall flush onto the capacitor layer 102 below new layer 102X. Arm 504 remains on top and remains squeezing the stack together between arm 504 and base pad 220.

Once the edges of layers 102X are down, upper members 234 and 236 are moved back into position to hold the stack in place and arm 504 is removed to get another layer if necessary. The process is repeated as many times as necessary. The stack can then be wrapped by a tape such as tape 204 and the capacitor stack can be further processed.

Thus, in summary, one embodiment of forming a capacitor stack includes placing a first capacitor layer in a fixture and onto a base pad which has a continually applied upward force applied to it such that the base pad forces the first layer upward while a pair of upper members proximate the upper portion of the fixture apply a downward force on the first layer so the first layer remains below the upper members and is squeezed between the upper members and the base pad. Then aligning and placing a second layer on top of the first layer by pressing a center of the second layer into a center of the first layer, and keeping the center pressure means in place while moving the upper members so that side edges of the second layer fall flush against the top surface of the first layer. Then moving the upper members back into place so that the upper members are now on top of the second layer and removing the center pressure means. Then repeatedly aligning and placing a plurality of capacitor layers onto the stack while continually applying the squeezing force on the stack, wherein each of the layers remains in its original alignment position.

One advantage of the system discussed above is that as the capacitor stack gets higher, minimal tilt is developed in the stack. This allows larger stacks to be manufactured quickly and easily. Moreover, the stacking system provides for greater anodic surface area since the anode surface area is optimized by not having to provide extraneous alignment notches in a capacitor case or other alignment features on the anode foil itself which decrease the anode surface area. Another advantage provided by the system is that an adhesive is not necessary between the layers of the capacitor stack. This saves time during the manufacturing process. Moreover, the present system allows a capacitor stack with non-standard edges, such as shown in FIG. 2 to be stacked and aligned without using any internal alignment features on the foil. In addition to flat capacitors, one or more embodiments of the present system can be used for forming stacks of thin, flimsy, material such as a battery stack.

Figure 10:
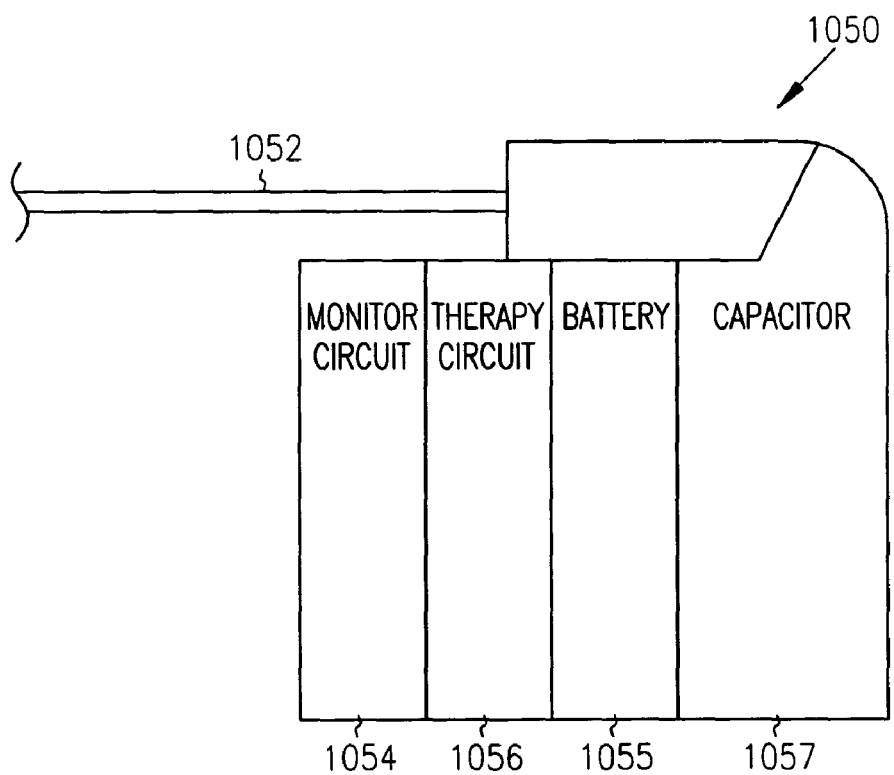
FIG. 10 shows a schematic representation of a defibrillator having a capacitor manufactured in accordance with one embodiment.

FIG. 10 schematically illustrates one of the many applications for a capacitor incorporating a capacitor stack manufactured as discussed above. One application includes an implantable medical device 1050 which provides therapeutic stimulus to a heart muscle, for instance, a defibrillator. The medical device 1050 is coupled with a lead system 1052. The lead system 1052 is implanted in a patient and electrically contacts strategic portions of a patient's heart. The medical device 1050 further includes a monitoring circuit 1054 for monitoring heart activity through one or more of the leads of the lead system 1052. The medical device 1050 further includes a therapy circuit 1056 which includes a battery 1055 and one or more capacitors 1057 manufactured in accordance with one embodiment of the system discussed above. The therapy circuit 1056 delivers a pulse of energy through one or more of the leads of lead system 1052 to the heart, where the medical device 1050 operates according to well known and understood principles.

In addition to implantable defibrillators and cardioverters, the capacitor can be incorporated into other cardiac rhythm management systems, such as heart pacers, combination pacer-defibrillators, congestive heart failure devices, and drug-delivery devices for diagnosing or treating cardiac arrhythmias. Moreover, the capacitor can be incorporated also into non-medical applications, for example, photographic flash equipment.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An apparatus for forming a capacitor stack for a flat capacitor, the apparatus comprising:

a fixture for holding a plurality of capacitor layers defining a capacitor stack as each of the plurality of capacitor layers is placed onto the capacitor stack;

means for continually applying a compression force on the capacitor stack until each of the plurality of capacitor layers have been placed onto the capacitor stack; and an alignment system for aligning each of the plurality of capacitor layers as each capacitor layer is place onto the capacitor stack, wherein the alignment system includes a vision alignment system.

2. The apparatus of claim 1, wherein the fixture includes a base pad for holding the capacitor stack, wherein the base pad is continually urged upwards.

3. The apparatus of claim 1, wherein means for continually applying a compression force includes a base pad for continually urging the capacitor stack upward and an upper member for contacting a top surface of the capacitor stack.

4. An apparatus for forming a capacitor stack, the apparatus comprising:

a fixture for holding a stack of individual capacitor layers, the fixture having a base pad and a force member to force the base pad upward, the fixture having an upper member to hold down the stack as the stack is forced upward by the base pad;

a placement member for placing each of a plurality of capacitor layers into the fixture; and an alignment system for aligning each of the plurality of capacitor layers as the placement member places each layer into the fixture, wherein the alignment system includes a vision alignment system;

wherein, the upper member is adapted to move while the placement member holds down each capacitor layer as each capacitor layer is placed onto the stack such that the stack is continually in compression.

5. The apparatus of claim 4, wherein the placement member includes a controlled robotic placement arm.

6. The apparatus of claim 4, wherein the force member includes a spring.

7. An apparatus comprising:

a base pad for holding a stack of individual capacitor layers;

a movable upper member located above the base pad, such that the stack is located between the base pad and the upper member;

a placement member for placing each of a plurality of capacitor layers onto the stack;

wherein, the upper member is adapted to move while the placement member holds down each capacitor layer as each capacitor layer is placed onto the stack such that the stack is continually held down by either the upper member or the placement member until each of the plurality of capacitor layers is placed; and an alignment system for aligning each of the plurality of capacitor layers as the placement member places each layer onto the stack, wherein the alignment system includes a vision alignment system.

8. The apparatus of claim 7, including a force member to force the base pad upwards towards the upper member.

9. The apparatus of claim 7, wherein the force member includes a spring.

* * * * *

UNITED STATES PATENT AND TRADEMARK OFFICE
CERTIFICATE OF CORRECTION

PATENT NO. : 7,089,982 B2 Page 1 of 1
APPLICATION NO. : 10/637604
DATED : August 15, 2006
INVENTOR(S) : Barr et al.

It is certified that error appears in the above-identified patent and that said Letters Patent is hereby corrected as shown below:

In column 7, line 6, in Claim 1, delete "place" and insert -- placed --, therefor.

Signed and Sealed this

Fourteenth Day of November, 2006

JON W. DUDAS
*Director of the United States Patent and Trademark Office*